(12) United States Patent
Isab et al.

(10) Patent No.: US 8,895,611 B1
(45) Date of Patent: Nov. 25, 2014

(54) CYTOTOXIC COMPOUNDS FOR TREATING CANCER

(71) Applicants: King Fahd University of Petroleum and Minerals, Dhahran (SA); King Abdulaziz City for Science and Technology, Riyadh (SA)

(72) Inventors: Anvarhusein Abdulkadir Isab, Dhahran (SA); Mohammed Ismail Mohammed Wazeer, Dhahran (SA); Said Salman Al-Jaroudi, Qatif (SA); Saleh Abdulaziz Altuwaijri, Al-Khobar (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 13/944,761

(22) Filed: Jul. 17, 2013

(51) Int. Cl.
*C07F 1/12* (2006.01)

(52) U.S. Cl.
CPC ..................................... *C07F 1/12* (2013.01)
USPC .......................................................... 514/495

(58) Field of Classification Search
None
See application file for complete search history.

(56) References Cited

U.S. PATENT DOCUMENTS

| 7,358,674 | B2 | 4/2008 | Bewlay et al. |
| 7,601,331 | B2 | 10/2009 | Chow et al. |
| 7,855,178 | B2 | 12/2010 | Alitalo et al. |
| 7,989,499 | B2 | 8/2011 | Anziano |
| 8,063,063 | B2 | 11/2011 | Sutton et al. |
| 8,324,225 | B2 | 12/2012 | Brain et al. |
| 2011/0027172 | A1 | 2/2011 | Wang et al. |
| 2011/0144163 | A1 | 6/2011 | Kingston et al. |
| 2011/0159111 | A1 | 6/2011 | Curry et al. |

OTHER PUBLICATIONS

Arsenijević et al. Cytotoxicity of gold(III) complexes on A549 Human Lung Carcinoma Epithelial Cell Line. Medicinal Chemistry, 2012, vol. 8, pp. 2-8.*
Buckley et al. Antitumor Properties of Some 2-[(Dimethylamino)methyl]phenylgold(III) Complexes. J. Med. Chem. 1996, 39, 5208-5217.*
Armstrong. Optical Isomer Separation by Liquid Chromatography. Anal. Chem. 1987, 59, 84A-91A.*
Tomuleasa, Ciprian et al., "Gold Nanoparticles Conjugated with Cisplatin/Doxorubicin/Capecitabine Lower the Chemoresistance of Hepatocellular Carcinoma-Derived Cancer Cells", Jun. 2012, Journal of Gastrointestinal and Liver Diseases, 21:187-196.
Ren, L. et al. (Jun. 2008) Cisplatin-Loaded Au-Au2S Nanoparticles for Potential Cancer Therapy: Cytotoxicity, In Vitro Carcinogenicity, and Cellular Uptake. *Journal of Biomedical Materials Research—Part A*, 85:787-796 (Abstract only).

* cited by examiner

*Primary Examiner* — Melenie McCormick
*Assistant Examiner* — Taina D Matos Negron
(74) *Attorney, Agent, or Firm* — Richard C. Litman

(57) ABSTRACT

The cytotoxic compounds are gold(III) complexes of the type [(diaminocyclohexane)AuCl$_2$]Cl, derived from sodium tetrachloroaurate(III) dihydrate NaAuCl$_4$.2H$_2$O. Specifically, the cytotoxic compounds are gold complexes of isomers of 1,2-diaminocyclohexane, namely cis-(±)-1,2-(diaminocyclohexane)AuCl$_3$, trans-(±)-1,2-(diaminocyclohexane)AuCl$_3$ and S,S-(+)-1,2-(diaminocyclohexane)AuCl$_3$. In order to treat cancer cells in a patient, such as human prostate cancer cells or human gastric cancer cells, an effective amount of the isomer of 1,2-(diaminocyclohexane)AuCl$_3$ is administered to the cancer cells in the patient. The isomer of 1,2-(diaminocyclohexane)AuCl$_3$ is preferably administered with a concentration ranging between about 10 μM and 20 μM.

3 Claims, 7 Drawing Sheets

CYTOTOXIC COMPOUNDS FOR TREATING CANCER

BACKGROUND OF THE INVENTION

1. Field of the Invention

The present invention relates to the treatment of cancer cells, such as human prostate cancer cells and human gastric cancer cells, and particularly to cytotoxic compounds for the treatment of cancer cells which are gold(III) complexes of the type [(diaminocyclohexane)AuCl$_2$] Cl.

2. Description of the Related Art

Cis-diamminedichloroplatinum(II) is an example of a commonly used platinum(II)-based anti-cancer drug. Continued usage of cis-diamminedichloroplatinum(II), unfortunately, has been found to lead to resistance to the drug in patients, along with a wide variety of undesirable side effects typically associated with chemotherapy treatments. Thus, alternative treatments which have the same efficacy of platinum(II)-based anti-cancer treatments are of great interest.

Gold(III) compounds have greatly attracted researchers' attention in the last decade for their outstanding cytotoxic actions. One such metal ion typically adopts a four-coordinate, square-planar geometry, thus is therefore expected to mimic the structural and electronic properties of platinum(II). Recent studies have shown that several gold(III) complexes are highly cytotoxic against different types of tumor cells, including some which are active even against the cis-diamminedichloroplatinum(II)-resistant cell lines.

The relationship to platinum(II) compounds makes gold (III) complexes good candidates for development and testing as anti-cancer drugs, although the relatively high kinetic ability and the often high redox potentials have largely hindered such investigations. In the early 1990's, a few gold compounds were prepared and characterized for their antitumor activity with positive results. Recently, using various Au(III) complexes with novel functionality has elicited further interest due to their distinct physical and chemical properties, stability under physiological conditions, and outstanding cytotoxic effects.

As noted above, cis-diamminedichloroplatinum(H) is one of the most widely used anti-cancer drugs today. However, platinum compounds possessing the 1,2-diaminocyclohexane (DACH) carrier ligand offer advantages over cis-diamminedichloroplatinum(II) with regard to bioavailability, activity and decreased renal toxicity. Over the past several years, significant effort has been devoted to study the antitumor activity of platinum-DACH complexes, whereas gold-DACH complexes have, up until now, received relatively little attention, despite the fact that Au(III) has a fairly rich biological chemistry. For example, Au(III) is redox active, can be coordinated by amino acids and proteins, is able to deprotonate and bind to the amide N of peptides, and is capable of cross-linking histidine imidazole rings.

As in the case of the parent cis-diamminedichloroplatinum (II), the antitumor activity of platinum-DACH is accompanied by some toxicity. The emergence of resistance and low water solubility that can affect the pharmacokinetics are additional features that must be improved in the quest for a more effective analog. Thus, it would be desirable to develop an anti-cancer treatment with the efficacy of platinum-DACH drugs, but with the preferable biological properties of Au(III).

Thus, cytotoxic compounds for treating cancer solving the aforementioned problems are desired.

SUMMARY OF THE INVENTION

The cytotoxic compounds are gold(III) complexes of the type [(diaminocyclohexane)AuCl$_2$]Cl, derived from sodium tetrachloroaurate(III) dihydrate NaAuCl$_4$.2H$_2$O. Specifically, the cytotoxic compounds are gold complexes of isomers of 1,2-diaminocyclohexane, namely cis-(±)-1,2-(DACH)AuCl$_3$ (referred to as compound 1 in the following), where DACH is diaminocyclohexane, having the following structure:

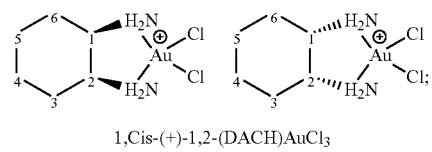

1,Cis-(+)-1,2-(DACH)AuCl$_3$ trans-(±)-1,2-(DACH)AuCl$_3$ (referred to as compound 2 in the following), having the following structure:

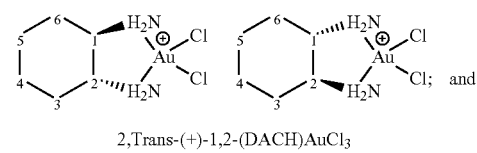

2,Trans-(+)-1,2-(DACH)AuCl$_3$ the purely optical active isomer (S,S)-(+)-1,2-(DACH)AuCl$_3$ (referred to as compound 3 in the following), having the following structure:

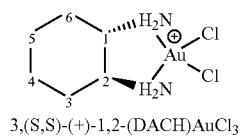

3,(S,S)-(+)-1,2-(DACH)AuCl$_3$

In order to treat cancer cells in a patient, such as human prostate cancer cells or human gastric cancer cells, an effective amount of the isomer of 1,2-(diaminocyclohexane) AuCl$_3$ is administered to the cancer cells in the patient. The isomer of 1,2-(diaminocyclohexane)AuCl$_3$ is preferably administered with a concentration ranging between about 10 μM and 20 μM.

These and other features of the present invention will become readily apparent upon further review of the following specification.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1A:
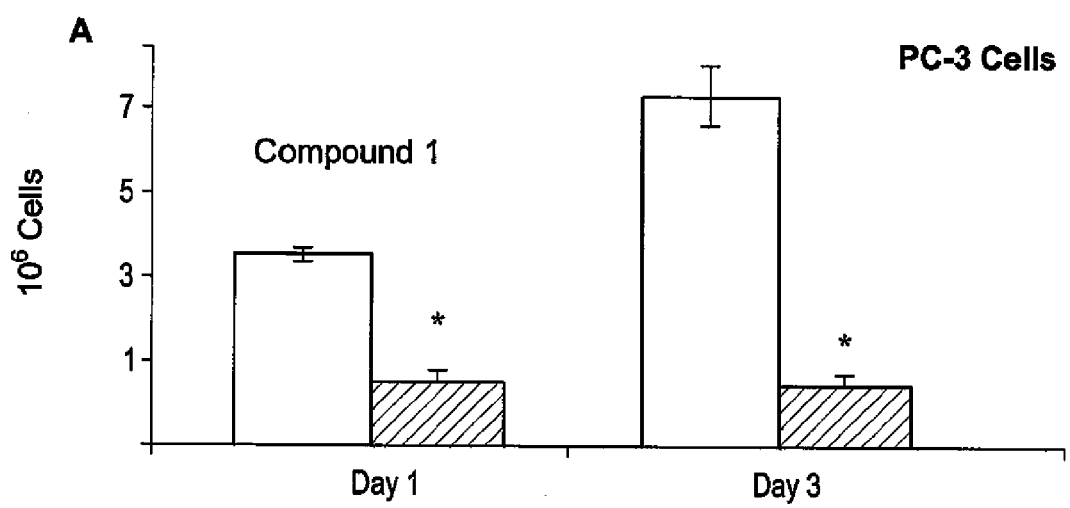
FIG. 1A illustrates the cell counts of human prostate cancer cells following treatment after both one and three days with the cytotoxic compound cis-(±)-1,2-(diaminocyclohexane) AuCl$_3$ with a concentration of 10 μM according to the present invention.

The cytotoxic compounds are gold(III) complexes of the type [(diaminocyclohexane)AuCl₂]Cl, derived from sodium tetrachloroaurate(III) dihydrate NaAuCl₄.2H₂O. Specifically, the cytotoxic compounds are gold complexes of isomers of 1,2-diaminocyclohexane. The isomerization structure of diaminocyclohexane is given by:

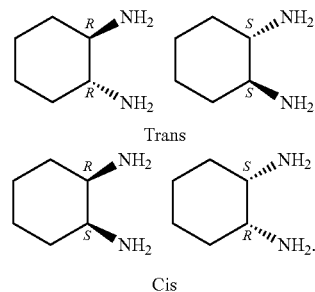

Trans

Cis

The present isomers are cis-(±)-1,2-(DACH)AuCl₃ (referred to as compound 1 in the following), where DACH is diaminocyclohexane, having the following structure:

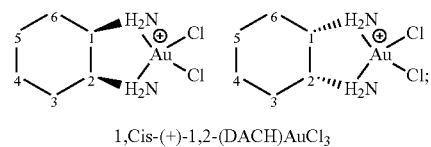

1,Cis-(+)-1,2-(DACH)AuCl₃ trans-(±)-1,2-(DACH)AuCl₃ (referred to as compound 2 in the following), having the following structure:

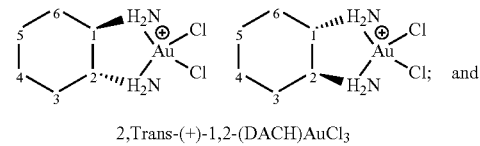

2,Trans-(+)-1,2-(DACH)AuCl₃ the purely optical active isomer (S,S)-(+)-1,2-(DACH)AuCl₃ (referred to as compound 3 in the following), having the following structure:

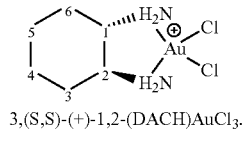

3,(S,S)-(+)-1,2-(DACH)AuCl₃.

Each of compounds 1, 2 and 3 were synthesized by dissolving of 0.50 mmol sodium tetrachloroaurate(III) dihydrateNaAuCl₄.2H₂O in a minimal amount of absolute ethanol at ambient temperature. In a separate beaker, a solution of 0.50 mmol of the diaminocyclohexane was prepared in a minimal amount of absolute ethanol. Both solutions were mixed (for a total volume of 40 mL) and stirred for about 30 minutes until a clear solution obtained. The clear solution was filtered and concentrated to 10 mL of solvent and then left to crystalize under refrigeration. The final solid yield was dried under vacuum, with yields ranging between 91% and 98%. Compounds 1, 2 and 3 were characterized by their physical properties, nuclear magnetic resonance (NMR), infrared (IR) and far-infrared studies, elemental analysis and X-ray crystallography. As will be shown below, all the data collected supported the formation of the desired DACH complexes. Melting points and elemental analysis for the three complexes are given below in Table 1.

TABLE 1

Melting Point and Elemental Analysis of Compounds 1, 2, and 3

| Compound | Melting point (° C.) | Found(Calc.)% | | |
|---|---|---|---|---|
| | | H | C | N |
| 1 | 201-206 | 3.35(3.38) | 17.22(17.26) | 6.67(6.71) |
| 2 | 170 deco. | 3.32(3.38) | 17.21(17.26) | 6.68(6.71) |
| 3 | 174 deco. | 3.29(3.38) | 17.18(17.26) | 6.65(6.71) |

Electronic spectra where obtained for the three diaminocyclohexane gold(III) complexes using a Lambda UV-Vis spectrophotometer, manufactured by PerkinElmer®, Inc. of Waltham, Mass. The resultant absorption data are shown below in Table 2.

TABLE 2

UV-Vis spectra $\lambda_{max}$ for Au(III) Complexes of Diaminocyclohexane

| Compound | $\lambda_{max}$ (nm) |
|---|---|
| $HAuCl_4$ | 320.0 |
| $NaAuCl_4$ | 292.5 |
| 1 | 302.5 |
| 2 | 301.6 |
| 3 | 301.5 |

The solid-state IR spectra of the ligands and their gold(III) complexes were recorded on an FTIR 180 spectrophotometer, manufactured by PerkinElmer®, Inc. of Waltham, Mass., using KBr pellets over the range 4000-400 $cm^{-1}$. The selected IR frequencies are given below in Table 3.

TABLE 3

IR frequencies, $v(cm^{-1})$ for Au(III)-(DACH) Complexes

| Complex | v(N—H) | $v_{shift}$ | v(C—N) | $v_{shift}$ |
|---|---|---|---|---|
| Cis-(±)-1,2-(DACH) | 3356 m, 3286 m | | 1092 s | |
| 1 | 3414 w | 93 | 1183 s | 91 |
| Trans-(±)-1,2-(DACH) | 3348 m, 3271 m, 3183 m | | 1082 m | |
| 2 | 3485 w, 3420 w, 3384 w | 137, 149, 201 | 1175 m | 93 |
| (S,S)-(+)-1,2-(DACH) | 3340 m, 3252 m, 3167 m | | 1082 m | |
| 3 | 3604 m, 3340 m, 3306 m | 364, 88, 139 | 1171 m | 89 |

Far-infrared spectra were recorded for compounds 1, 2 and 3 at 4 $cm^{-1}$ resolution at room temperature as cesium chloride discs on a Nicolet® 6700 FT-IR spectrometer with a far-IR beam splitter, manufactured by Thermo Electron Scientific Instruments, LLC of Madison, Wis. Far-IR data for the three compounds are given below in Table 4.

TABLE 4

Far IR frequencies, $v(cm^{-1})$ for Compounds 1, 2, and 3

| Species | Au—Cl | Au—N |
|---|---|---|
| $NaAuCl_4$ | 369 | |
| 1 | 352, 367 | 437 |
| 2 | 353, 365 | 437 |
| 3 | 353, 366 | 395, 436 |

All NMR measurements were performed on a Jeol® JNM-LA 500 NMR spectrophotometer, manufactured by Jeol, Ltd. of Tokyo, Japan, at 297 K. The $^1H$ NMR spectra were recorded at a frequency of 500.00 MHz. The $^{13}C$ NMR spectra were obtained at a frequency of 125.65 MHz with $^1H$ broadband decoupling and referenced relative to TMS. The spectral conditions were: 32,000 data points, a 0.967 second acquisition time, a 1.00 second pulse delay and a 45° pulse angle. The $^1H$ and $^{13}C$ NMR chemical shifts are given below in Table 5 and Table 6, respectively.

TABLE 5

$^1H$ NMR chemical shifts of free ligands and Au(III) cyclohexanediamine complexes in $CD_3OD$

| | $^1H$(δ in ppm) | | | | |
|---|---|---|---|---|---|
| Compound | H1, H2 | H3, H6 (eq) | H3, H6 (ax) | H4, H5 (eq) | H4, H5 (ax) |
| Cis-(±)-1,2-(DACH) | 2.23, m | 1.85, m | 1.69, m | 1.28, m | 1.12, m |
| Trans-(±)-(DACH) | 2.25, m | 1.85, m | 1.68, m | 1.28, m | 1.11, m |
| (1S,2S)-(+)- 1,2-(DACH) | 2.24, m | 1.85, m | 1.69, m | 1.28, in | 1.11, m |
| 1 | 3.59, m | 2.02, m | 1.79, m | 1.76, m | 1.47, m |
| 2 | 3.04, m | 2.18, m | 1.69, m | 1.54, m | 1.22, m |
| 3 | 3.09, m | 2.20, m | 1.67, m | 1.55, m | 1.22, m |

TABLE 6

$^{13}C$ NMR chemical shifts of free ligands and Au(III) cyclohexanediamine complexes in $CD_3OD$

| | $^{13}C$(δ in ppm) | | |
|---|---|---|---|
| Compound | C1, C2 | C3, C6 | C4, H5 |
| Cis-(±)-1,2-(DACH) | 58.20 | 35.26 | 26.36 |
| Trans-(±)-(DACH) | 58.46 | 35.55 | 26.63 |
| (1S,2S)-(+)- 1,2-(DACH) | 58.27 | 35.32 | 26.43 |
| 1 | 63.33 | 26.78 | 21.43 |
| 2 | 65.87 | 33.58 | 24.85 |
| 3 | 65.94 | 33.47 | 24.65 |

$^{13}C$ solid-state NMR spectra were performed on a Bruker® 400 MHz spectrometer, manufactured by the Bruker Medizintechnik GmbH Corporation of Rheinstetten, Germany, at ambient temperature of 25° C. Samples were packed into 6 mm zirconium oxide rotors. Cross polarization and high power decoupling were employed. A pulse delay of 7.0 seconds and a contact time of 5.0 ms were used in the CPMAS experiments. The magic angle spinning rates were 4 and 8 kHz. Carbon chemical shifts were referenced to TMS by setting the high frequency isotropic peak of solid adarnantane to 38.56 ppm. The solid NMR data are given below in Table 6B.

TABLE 7

Solid 13C NMR chemical shifts of free ligands and Au(III) cyclohexanediamine complexes

| | $^{13}C$(δ in ppm) | | |
|---|---|---|---|
| Compound | C1, C2 | C3, C6 | C4, H5 |
| 1 | 69.20, 65.35 | 30.98 | 27.02, 22.12 |
| 2 | 69.60 | 37.37 | 27.99 |
| 3 | 70.21 | 37.86 | 29.16 |

For X-ray crystallography analysis, an X-ray quality single crystal, obtained from an EtOH solution, was mounted in a thin-walled glass capillary on a Bruker®-Axs Smart Apex diffractometer, manufactured by the Bruker Medizintechnik GmbH Corporation of Rheinstetten, Germany, equipped with a graphite mono chromatized Mo Kα radiation (λ=0.71073 Å). The data were collected using the SMART software of the Bruker®-Axs Smart Apex diffractometer. The data integration was performed using the SAINT software of the Bruker®-Axs Smart Apex diffractometer. An empirical absorption correction was carried out using SADABS software produced by the University of Gottingen in Germany for empirical absorption correction of area detector data. The structure was solved with direct methods and refined by full matrix least square methods based on $F^2$, using the structure determination software, SHELXTL, of the Bruker®-Axs Smart Apex diffractometer. For compound 1, some of the hydrogen atoms of the disordered ethanol molecule could not be placed. For compound 2, one hydrogen atom of the water molecule was located on a Fourier difference map and refined isotropically, and the second one could not be placed reliably. All other H atoms were placed at calculated positions using a riding model. Crystal and structure refinement data are given below in Table 8. Selected bond lengths and bond angles are given in Table 9.

TABLE 8

Crystal and Structure Refinement Data for Compounds 1 and 2

| Compound | 1 | 2 |
|---|---|---|
| CCDC deposit no. | 831613 | 850216 |
| Empirical formula | $C_{14}H_{34}Au_2Cl_6N_4O$ | $C_{12}H_{30}Au_2Cl_6N_4O$ |
| Formula weight | 881.09 | 853.03 |
| Temperature (K) | 297(2) | 295(2) |
| Wavelength (Å) | 0.71073 | 0.71073 |
| Crystal system | Orthorhombic | Monoclinic |
| Space group | Pbcn | $P2_1$ |
| Unit cell dimensions | | |
| a (Å) | 19.792(1) | 9.5898(7) |
| b (Å) | 12.4662(7) | 8.6106(6) |
| c (Å) | 10.3212(6) | 14.477(1) |
| β (°) | | 95.307(1) |
| Volume (Å³) | 2546.5(2) | 1190.3(2) |
| Z | 4 | 2 |
| Calc. density (g.cm⁻³) | 2.298 | 2.38 |
| Absorp. coefficient (mm⁻¹) | 12.152 | 12.994 |
| F(000) | 1656 | 796 |
| Crystal size (mm) | 0.40 × 0.37 × 0.26 | 0.52 × 0.49 × 0.16 |
| θ range (°) | 1.93-28.29 | 1.41-28.28 |
| Limiting indices | −26 ≤ h ≤ 26 | −12 ≤ h ≤ 12 |
| | −16 ≤ k ≤ 16 | −11 ≤ k ≤ 11 |
| | −13 ≤ l ≤ 13 | −19 ≤ l ≤ 19 |
| Max and min transmission | $T_{min}$ = 0.0850, $T_{max}$ = 0.1443 | $T_{min}$ = 0.0564, $T_{max}$ = 0.2244 |
| Data/restraints/parameters | 3162/0/128 | 5835/2/230 |
| Goodness-of-fit on $F^2$ | 1.051 | 1.017 |
| Final R indices [I > 2σ(I)] | $R_1$ = 0.0246, $wR_2$ = 0.0631 | $R_1$ = 0.0308, $wR_2$ = 0.0739 |
| R indices (all data) | $R_1$ = 0.0288, $wR_2$ = 0.0654 | $R_1$ = 0.0329, $wR_2$ = 0.0747 |
| Largest diff. Peak and hole (e Å⁻³) | 1.766 and −1.544 | 0.796 and −1.555 |

TABLE 9

Selected Bond Lengths (Å) and Bond Angles (°) for Compounds 1 and 2

| 1 | 2 | |
|---|---|---|
| Au1—N1 2.029(4) | Au1—N1 2.029(6) | Au2—N3 2.029(6) |
| Au1—N2 2.030(3) | Au1—N2 2.031(5) | Au2—N4 2.054(7) |
| Au1—Cl1 2.261(1) | Au1—Cl1 2.274(2) | Au2—Cl3 2.259(3) |
| Au1—Cl2 2.268(1) | Au1—Cl2 2.276(2) | Au2—Cl4 2.266(2) |
| N1—Au1—N2 83.9(2) | N1—Au1—N2 84.3(3) | N3—Au2—N4 84.1(2) |
| N1—Au1—Cl1 91.7(1) | N1—Au1—Cl1 92.0(2) | N3—Au2—Cl3 92.2(2) |
| N2—Au1—Cl1 175.4(1) | N2—Au1—Cl1 176.2(2) | N4—Au2—Cl3 176.2(2) |
| N1—Au1—Cl2 176.0(1) | N1—Au1—Cl2 174.2(2) | N3—Au2—Cl4 176.4(2) |
| N2—Au1—Cl2 92.6(1) | N2—Au1—Cl2 89.9(2) | N4—Au2—Cl4 92.3(2) |
| Cl1—Au1—Cl2 91.83(5) | Cl1—Au1—Cl2 93.81(8) | Cl3—Au2—Cl4 91.4(1) |

Figure 1B:
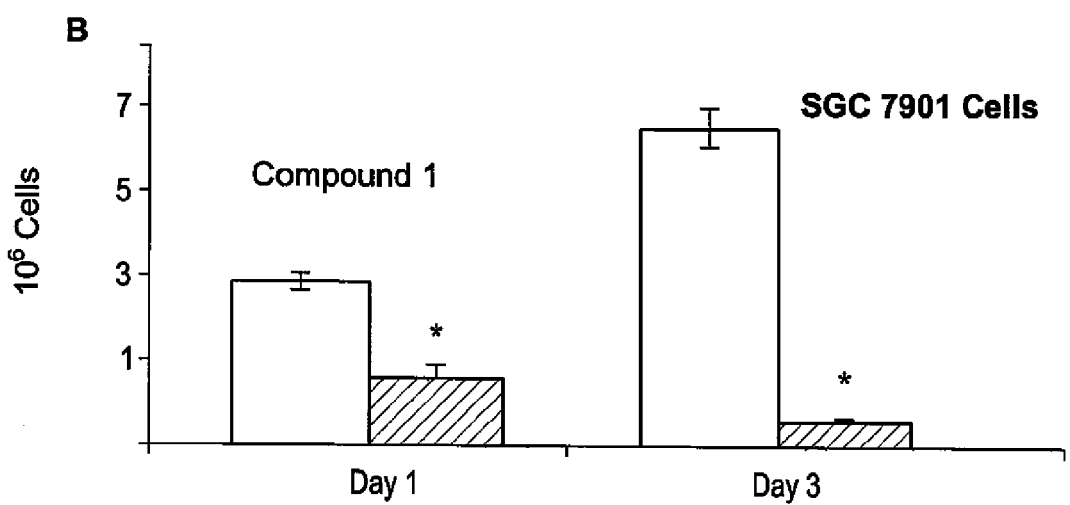
FIG. 1B illustrates the cell counts of human gastric cancer cells following treatment after both one and three days with the cytotoxic compound cis-(±)-1,2-(diaminocyclohexane) AuCl$_3$ with a concentration of 10 μM according to the present invention.
Figure 2A:
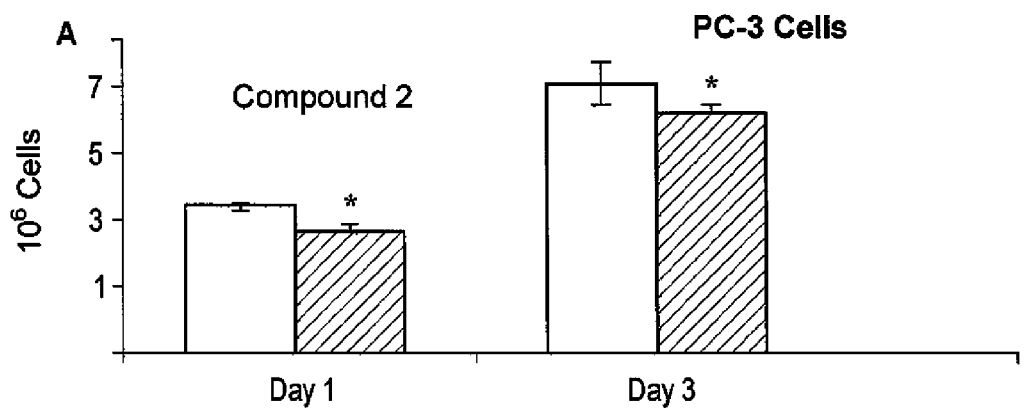
FIG. 2A illustrates the cell counts of human prostate cancer cells following treatment after both one and three days with the cytotoxic compound trans-(±)-1,2-(diaminocyclohexane) AuCl$_3$ with a concentration of 10 μM according to the present invention.
Figure 2B:
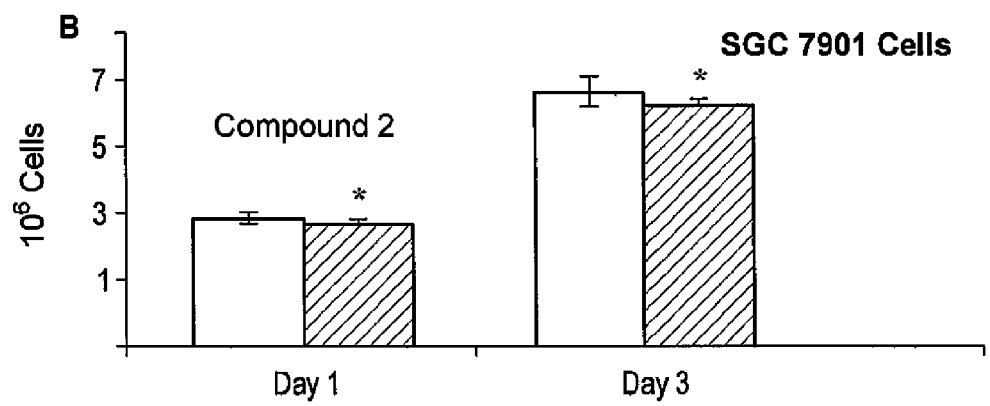
FIG. 2B illustrates the cell counts of human gastric cancer cells following treatment after both one and three days with the cytotoxic compound trans-(±)-1,2-(diaminocyclohexane) AuCl₃ with a concentration of 10 μM according to the present invention.
Figure 3A:
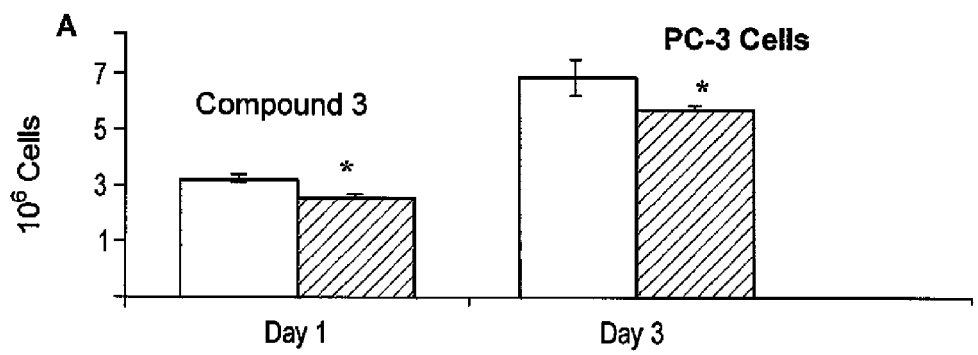
FIG. 3A illustrates the cell counts of human prostate cancer cells following treatment after both one and three days with the cytotoxic compound S,S-(+)-1,2-(diaminocyclohexane) AuCl₃ with a concentration of 10 μM according to the present invention.
Figure 3B:
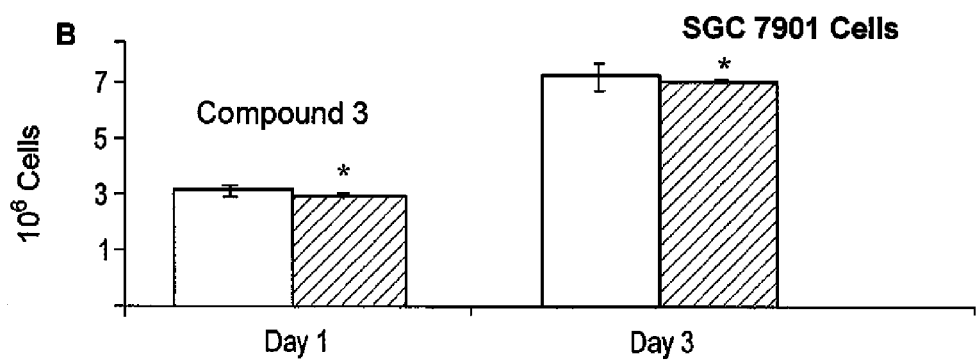
FIG. 3B illustrates the cell counts of human gastric cancer cells following treatment after both one and three days with the cytotoxic compound S,S-(+)-1,2-(diaminocyclohexane) AuCl₃ with a concentration of 10 μM according to the present invention.

In order to test the efficacy of the cytotoxic compounds 1, 2 and 3 in treating cancer cells, both human gastric cancer cells (SGC-7901) and prostate cancer cells (PC-3) were incubated. Trypan blue dye exclusion analysis and MTT assay were used to detect cell proliferation and assess the inhibitory effect of compounds 1, 2 and 3 on the proliferation of SGC-7901 and PC-3 cells. In one culture plate, human gastric cancer SGC-7901 and PC-3 cells were treated with various concentrations of compounds 1, 2 and 3, along with water, used as a control. The results are shown in FIGS. 1A-3B. FIGS. 1A and 1B illustrate the cell counts of PC-3 cells and SGC 7901 cells, respectively, after both one and three days of treatment with cis-(±)-1,2-(DACH)AuCl₃ (i.e., compound 1). FIGS. 2A and 2B illustrate the cell counts of PC-3 cells and SGC 7901 cells, respectively, after both one and three days of treatment with trans-(±)-1,2-(DACH)AuCl₃ (i.e., compound 2). FIGS. 3A and 3B illustrate the cell counts of PC-3 cells and SGC 7901 cells, respectively, after both one and three days of treatment with S,S-(+)-1,2-(DACH)AuCl₃ (i.e., compound 3). The results in FIGS. 1A-3B are expressed as the mean, SD (p<0.05). In FIGS. 1A-3B, the cells were treated with a concentration of 10 μM of each compound.

Figure 4A:
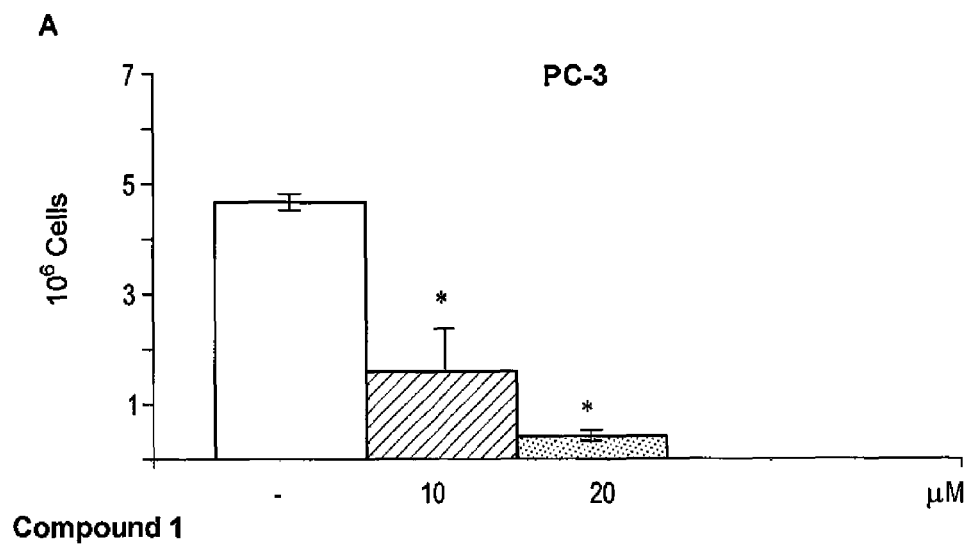
FIG. 4A illustrates the cell counts of human prostate cancer cells following treatment for one full day with concentrations of both 10 μM and 20 μM for the cytotoxic compound cis-(±)-1,2-(diaminocyclohexane)AuCl₃ according to the present invention.
Figure 4B:
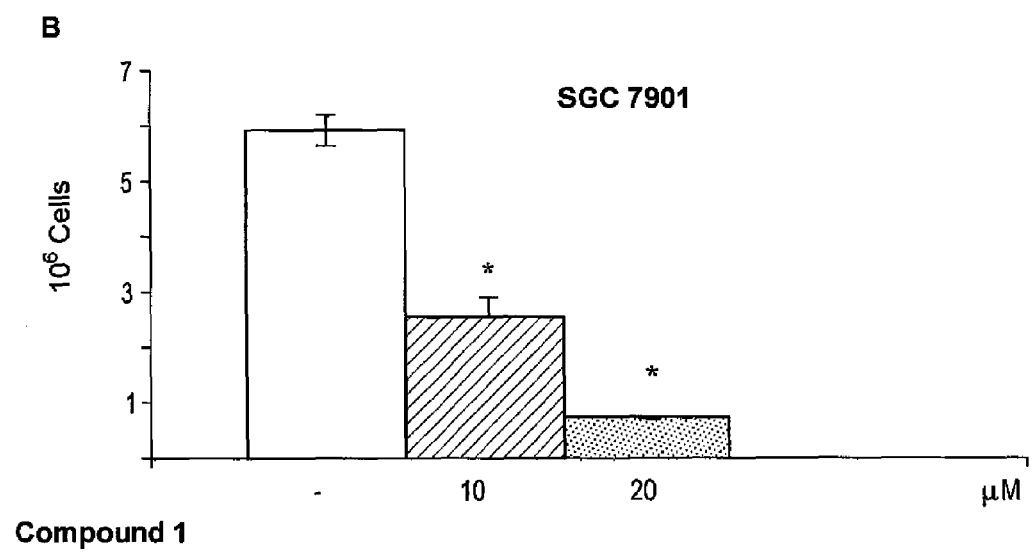
FIG. 4B illustrates the cell counts of human gastric cancer cells following treatment for one full day with concentrations of both 10 μM and 20 μM for the cytotoxic compound cis-(±)-1,2-(diaminocyclohexane)AuCl₃ according to the present invention.
Figure 5A:
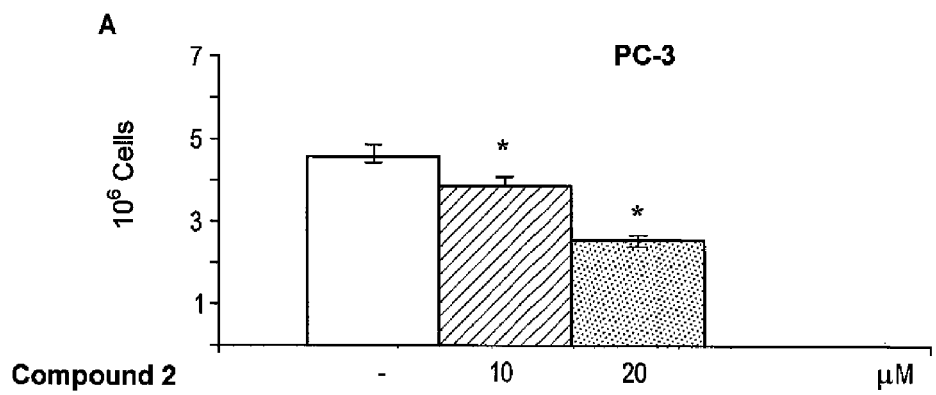
FIG. 5A illustrates the cell counts of human prostate cancer cells following treatment for one full day with concentrations of both 10 μM and 20 μM for the cytotoxic compound trans-(±)-1,2-(diaminocyclohexane)AuCl₃ according to the present invention.
Figure 5B:
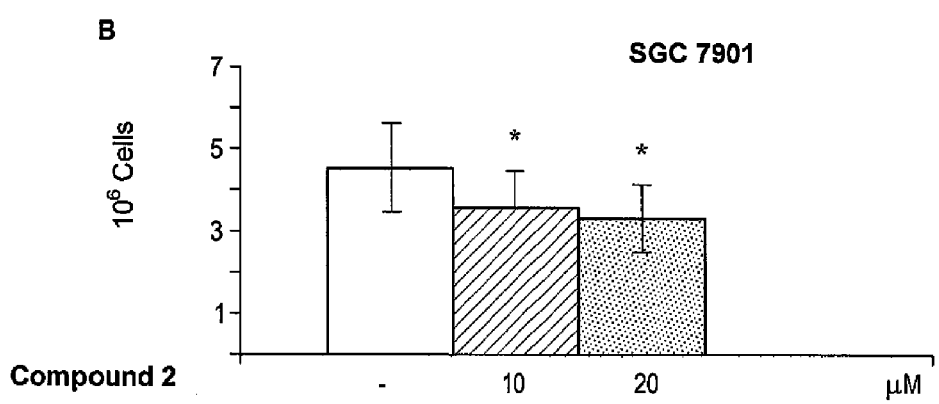
FIG. 5B illustrates the cell counts of human gastric cancer cells following treatment for one full day with concentrations of both 10 μM and 20 μM for the cytotoxic compound trans-(±)-1,2-(diaminocyclohexane)AuCl₃ according to the present invention.
Figure 6A:
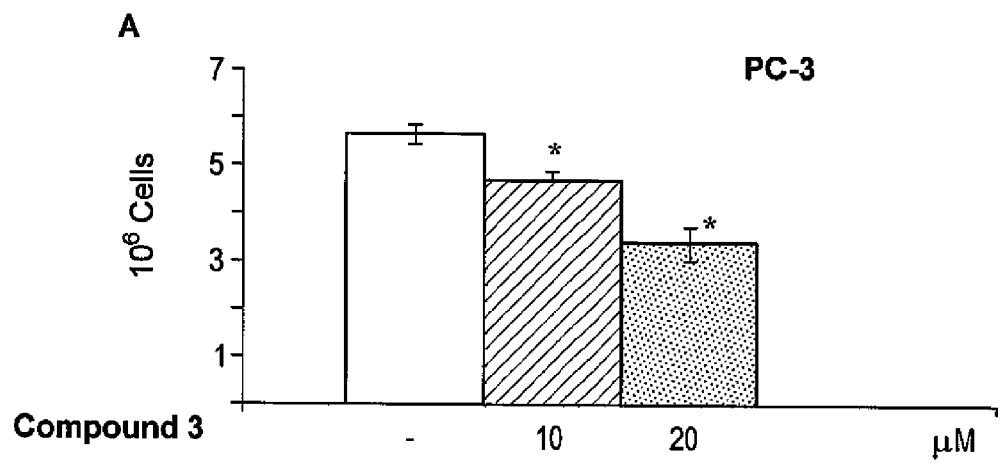
FIG. 6A illustrates the cell counts of human prostate cancer cells following treatment for one full day with concentrations of both 10 μM and 20 μM for the cytotoxic compound S,S-(+)-1,2-(diaminocyclohexane)AuCl₃ according to the present invention.
Figure 6B:
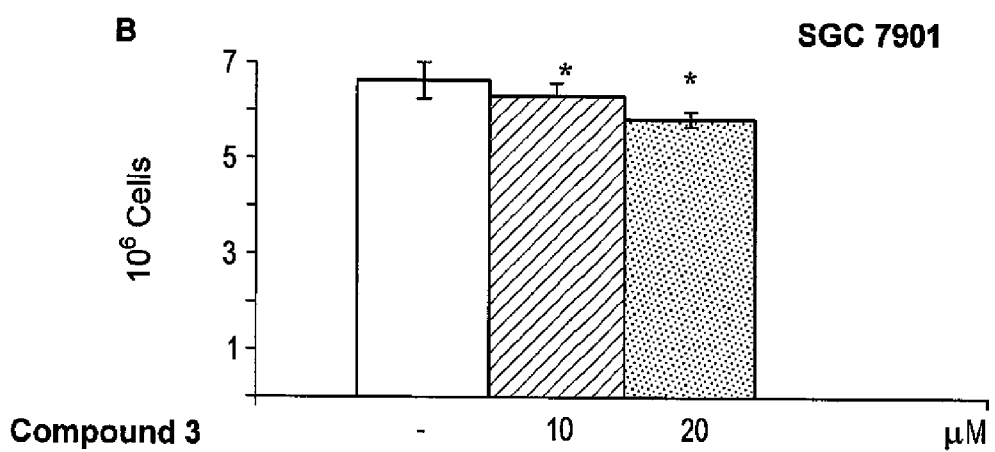
FIG. 6B illustrates the cell counts of human gastric cancer cells following treatment for one full day with concentrations of both 10 μM and 20 μM for the cytotoxic compound S,S-(+)-1,2-(diaminocyclohexane)AuCl₃ according to the present invention.
Figure 7A:
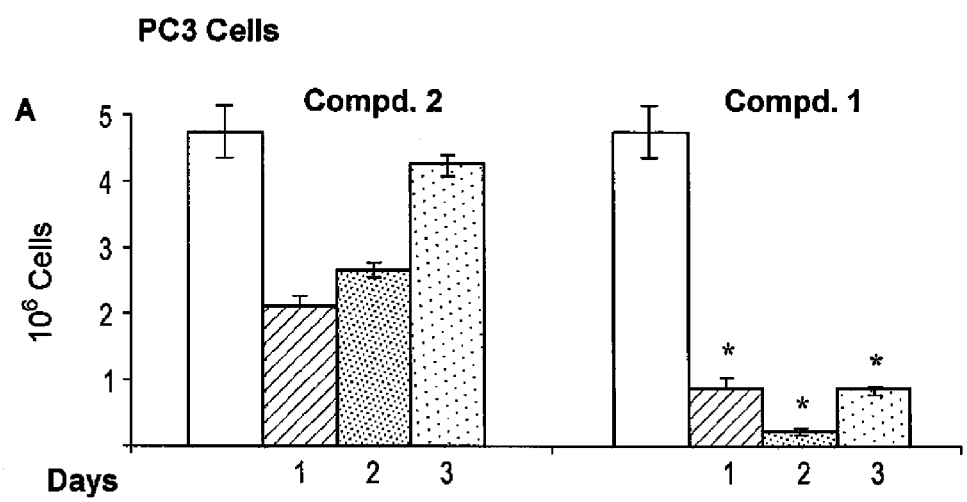
FIG. 7A illustrates a comparison of the cell counts of human prostate cancer cells following treatment for one, two and three days with a concentration of 10 μM for the cytotoxic compounds trans-(±)-1,2-(diaminocyclohexane)AuCl₃ and cis-(±)-1,2-(diaminocyclohexane)AuCl₃ according to the present invention.
Figure 7B:
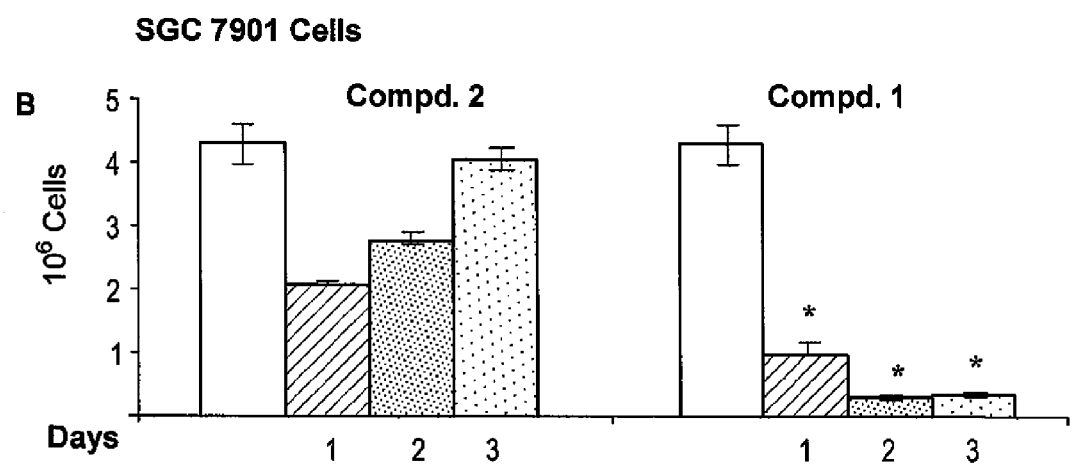
FIG. 7B illustrates a comparison of the cell counts of human gastric cancer cells following treatment for one, two and three days with a concentration of 10 μM for the cytotoxic compounds trans-(±)-1,2-(diaminocyclohexane)AuCl₃ and cis-(±)-1,2-(diaminocyclohexane)AuCl₃ according to the present invention.

FIGS. 4A and 4B illustrate the cell counts of PC-3 cells and SGC 7901 cells, respectively, after one full day (24 hours) of treatment with cis-(±)-1,2-(DACH)AuCl₃ (i.e., compound 1)

using concentrations of both 10 μM and 20 μM for the compound. FIGS. 5A and 5B illustrate the cell counts of PC-3 cells and SGC 7901 cells, respectively, after one full day (24 hours) of treatment with trans-(±)-1,2-(DACH)AuCl$_3$ (i.e., compound 2) using concentrations of both 10 μM and 20 μM for the compound. FIGS. 6A and 6B illustrate the cell counts of PC-3 cells and SGC 7901 cells, respectively, after one full day (24 hours) of treatment with S,S-(+)-1,2-(DACH)AuCl$_3$ (i.e., compound 3) using concentrations of both 10 μM and 20 μM for the compound. The results in FIGS. 4A-6B are expressed as the mean, SD (p<0.05). In FIGS. 7A and 7B, compound 2 is compared against compound 1 in the treatment of PC-3 cells and SGC 7901 cells, respectively, with results being shown following one, two and three days of treatment with a concentration of 10 μM for each compound. The anti-proliferative effect was measured by MTT assay. Results are expressed as the mean, SD (p<0.05).

In the assessment of cell proliferation, the SGC-7901 and PC-3 cells were seeded on 96-well plates at a predetermined optimal cell density to ensure exponential growth in the duration of the assay. After 24 hours of pre-incubation, the growth medium was replaced with an experimental medium containing the appropriate compound (i.e., compound 1, 2 or 3) or the control. Six duplicate wells were set up for each sample, and cells untreated with a compound served as a control. Treatment was conducted at 24 and 72 hours, respectively. After incubation, 10 μL MTT (6 g/L, Sigma) was added to each well and the incubation was continued for 4 hours at 37° C. After removal of the medium, MTT stabilization solution (dimethylsulphoxide: ethanol=1:1) was added to each well, and shaken for ten minutes until all crystals were dissolved. Then, optical density was detected in a micro plate reader at 550 nm wavelength using an enzyme-linked immunosorbent assay (ELISA) reader. Each assay was performed in triplicate. Cell number and viability were determined by trypan blue dye exclusion analysis.

With regard to the electronic spectra, the $\lambda_{max}$ values for the complexes are shown above in Table 2. The Au(III) complexes show absorption in the region 250-350 nm (40,000-28,570 cm$^{-1}$), which correspond to LMCT transitions signals at 300 nm that could be assigned to Cl→Au charge transfer by analogy to auric acid absorption spectra, which give a band at 320 nm, where this transition of high extinction coefficient cannot be assigned to the symmetry-forbidden d-d transition. According to crystal field theory for d$^8$ complexes, the LUMO orbital is d$_{x2-y2}$, so ligand to metal charge transfer could be due to p$_\sigma$→d$_{x2-y2}$ transition. It is evident that the electronic spectra of these compounds are stable and consistent, which means that the gold center remains in the +3 oxidation states.

With regard to the IR and Far-IR spectroscopic analysis, Table 3 above lists the significant IR bands of free DACH ligand and their Au(III) complexes. The N—H stretching band, which occurs around 3300 cm$^{-1}$ for the free ligands, shifts towards higher frequency (blue shift) upon complexation by about 150 cm$^{-1}$. Another important vibrational band observed in IR spectra is C—N stretching, which also showed a slight shift to higher wave number, indicating a shorter C—N bond in the complex than in the free ligand. Far-IR showed absorption bands at 353 and 367 cm$^{-1}$ for symmetric and asymmetric stretching of the Au—Cl, which is consistent with Au—Cl stretching mode trans to nitrogen. Another group of bands at 395 and 437 cm$^{-1}$ could be assigned for the symmetric and asymmetric stretching of the Au—N bond. The red shift of the DACH complexes with respect to the auric acid shows the weakening of the Au—Cl bond.

With regard to NMR characterization, the $^1$H and $^{13}$C NMR chemical shifts of compounds 1, 2 and 3, along with their corresponding free ligand, are listed above in Tables 5, 6 and 7, respectively. Also, the $^1$H and $^{13}$C NMR spectra of complexes 1, 2 and 3 depicted one half of the total expected signals due to the C$_2$ symmetry axis. The 1,2-diaminocyclohexane ring is considered as a rigid conformer that allowed for the distinguishing of the equatorial H3 and H4 from the axial H3 and H4 at room temperature. $^1$H NMR downfield shift was observed for complexes with respect to the free diamine ligands. The significant downfield shift was observed at 3.59 ppm for complex 1 with respect to the free DACH ligand at 2.23 ppm. This can be attributed to the donation of nitrogen lone pairs to the gold, which causes de-shielding of the proton(s) next to the bonding nitrogen. On the other hand, $^{13}$C NMR downfield shift was observed only for the carbon next to the bonding nitrogen, and the other carbons in the complex showed upfield shift. For example, chemical shift of C3 and C4 for complex 1 was observed at 26.78 and 21.43 ppm, respectively, whereas, for free diamine ligand, it occurred at 35.26 and 26.36 ppm. It should be noted that even though compounds 1, 2 and 3 have same skeleton as that of DACH, their NMR chemical shifts are not the same, due to differences in their stereochemistry upon complexation.

With regard to solid-state NMR, at the spinning rate of 8 kHz, only the isotropic signals were observed for the carbons, indicating small anisotropy due to the sp$^3$ hybridization of these atoms. Compared to solution chemical shifts, substantial de-shielding in solid state is observed with similarity in the chemical shift among all synthesized complexes, as shown above in Table 8, which is a clear indication of stability of the prepared complexes. Solid state NMR spectrum of compound 1 showed two sets of peaks with equal intensity, which supports the non-equivalence of all six carbon atoms of DACH. This indicates that compound 1 in the solid state lacks C$_2$ symmetry.

With regard to the X-ray crystal structure for compound 1, the gold(III) ion is bonded to two nitrogen atoms of the cis-cyclohexane-1,2-diamine ligand and two chloride ions in a distorted square planar geometry. The two Au—N bond distances are not significantly different (2.029(4) Å), while the Au—Cl bond distances are 2.261(1) Å and 2.268(1) Å, respectively, as given above in Tables 8 and 9. The Cl—Au—Cl and N—Au—N bond angles are 91.83(5)° and 83.9(2)°, respectively. The latter value reflects the chelation strain of the diamine ligand. These values are similar to those found in dichloro-(ethylenediamine-N,N')-gold(III) chloride dehydrate and dichloro-(1,2-ethanediamine)-gold(III) nitrate. The cyclohexyl ring adopts a chair conformation. The square planar geometry and the five-membered ring strain impose a torsion angle N1-C1-C2-N2 of 49.80°. All amine hydrogen atoms are engaged in hydrogen bonding with the Cl$^-$ counter ion. A molecule of ethanol is present in the lattice, which presents an orientation disorder on a two-fold rotation axis. The metal complex molecules pack head to tail to generate molecular chains along the c-axis, which, in turn, pack into layers, parallel to the ac-plane. These are separated by sheets hosting columns of disordered ethanol molecules and Cl$^-$ counter ions having hydrogen bonding interactions with the NH$_2$ groups of adjacent layers.

In compound 2, the asymmetric unit contains two cationic molecules of the gold complex, two chloride counter ions and one crystallization water molecule. Similar to that of compound 1, the gold(III) ion is bonded to two nitrogen atoms of the trans-cyclohexane-1,2-diamine ligand and two chloride ions. The geometry is distorted as square planar with Au—N and Au—Cl bond distances in the ranges of 2.029(6)-2.054

(7) Å and 2.259(3)-2.276(2) Å, respectively, with similar N—Au—N bond angles of 84.1(2)° in addition to Cl—Au—Cl bond angles in the range 91.4(1)°-93.81(8)°. The coordination sphere bond distances and bond angles are similar to those of compound 1. The two cyclohexyl rings adopt a chair conformation with N1-C1-C6-N2 and N3-C7-C12-N4 torsion angles of 55.78° and 52.33°, respectively. Hydrogen bonding interactions take place between the amino groups and the chloride counter ions.

With regard to the effect of compounds 1, 2 and 3 on cell proliferation, the bioassay tests were completed for compounds 1, 2 and 3 under various experimental conditions. The cytotoxicity assay was performed with various concentrations of the synthesized gold (III) complexes on PC-3 and SGC-7901 cells. The experimental PC-3 and SGC-7901 cells were treated with various concentrations of compounds 1, 2 and 3 for 24-72 hours and the cell viability was determined as described above by MTT assay. These results are shown above in Tables 5, 6 and 7, along with FIGS. 1A-7B. As shown in FIGS. 1A-3B, the cis-($\pm$)-1,2-(DACH)-gold complex exhibited potentially high activity against gastric cancer cells SGC-7901 and human prostate cancer cells after 24 and 72 hours of treatment with the compound at a concentration of 10 $\mu$M. Whereas, trans-($\pm$)-1,2-(DACH) and purely chiral trans-(−)-1,2-(DACH) gold complexes showed moderate inhibition against SGC-7901 and PC-3 cell lines under the same assay experimental condition. From FIGS. 4A-6B, it can be seen that the gold(III) complexes showed concentration-dependent cytotoxic effects on cancerous cells PC-3 and SGC-7901. It can be concluded that there is no significant difference in the bioactivity between trans-(1R,2R)-(DACH) isomer and trans-(1S,2S)-(DACH) isomer.

In the time-dependent activity studies, it was seen that after 72 hours of the experiment with compound 1 on PC-3 cells, the cell proliferation is bit higher than that of the SGC-7901 cells at fixed 10 $\mu$M concentration (FIGS. 1A and 1B). Furthermore, in FIGS. 7A and 7B, the cytotoxicity results demonstrate that compound 1 at a concentration of 10 $\mu$M has higher cytotoxic effect in comparison with the same concentration of compound 2.

It is to be understood that the present invention is not limited to the embodiments described above, but encompasses any and all embodiments within the scope of the following claims.

We claim:

1. A composition consisting of a cytotoxic compound wherein the cytotoxic compound is cis-($\pm$)-1,2-(diaminocyclohexane)AuCl$_3$.

2. A method for treating prostate or gastric cancer cells in vitro comprising the step of administering an effective amount of a composition consisting of a cytotoxic compound wherein the cytotoxic compound is cis-($\pm$)-1,2-(diaminocyclohexane)AuCl$_3$.

3. The method for treating prostate or gastric cancer cells in vitro as recited in claim 2, wherein the step of administering the effective amount comprises administering the effective amount of a composition consisting of a cytotoxic compound wherein the cytotoxic compound is cis-($\pm$)-1,2-(diaminocyclohexane)AuCl$_3$ at a concentration in the range of about 10 $\mu$M to 20 $\mu$M.

* * * * *